(12) United States Patent
Jennewine

(10) Patent No.: US 8,512,244 B2
(45) Date of Patent: Aug. 20, 2013

(54) INTEGRATED ANALYTE SENSOR AND INFUSION DEVICE AND METHODS THEREFOR

(75) Inventor: R. Curtis Jennewine, San Francisco, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 295 days.

(21) Appl. No.: 12/238,902

(22) Filed: Sep. 26, 2008

(65) Prior Publication Data

US 2009/0069650 A1    Mar. 12, 2009

Related U.S. Application Data

(62) Division of application No. 11/428,299, filed on Jun. 30, 2006.

(51) Int. Cl.
*A61B 5/00* (2006.01)
*A61M 31/00* (2006.01)

(52) U.S. Cl.
USPC ........... 600/365; 600/309; 604/503; 604/504; 604/506

(58) Field of Classification Search
USPC ............... 600/309, 345–366; 604/503, 504, 604/506
See application file for complete search history.

(56) References Cited

U.S. PATENT DOCUMENTS

| | | | |
|---|---|---|---|
| 571,761 A | 11/1896 | Gulliford | |
| 1,555,351 A | 9/1925 | Boynton | |
| 2,587,707 A | 3/1950 | Dever | |
| 2,755,036 A | 7/1956 | Mikko | |
| 3,208,121 A | 9/1965 | Price | |
| 3,923,060 A * | 12/1975 | Ellinwood, Jr. | 604/891.1 |
| 3,924,819 A | 12/1975 | Lapinskas | |
| 4,003,379 A * | 1/1977 | Ellinwood, Jr. | 604/891.1 |
| 4,055,175 A | 10/1977 | Clemens et al. | |
| 4,076,182 A | 2/1978 | Stites | |
| 4,151,845 A | 5/1979 | Clemens | |
| 4,360,019 A | 11/1982 | Portner | |
| 4,387,863 A | 6/1983 | Edmonston | |
| 4,601,707 A | 7/1986 | Albisser et al. | |
| 4,629,145 A | 12/1986 | Graham | |
| 4,667,896 A | 5/1987 | Frey et al. | |
| 4,685,903 A | 8/1987 | Cable et al. | |
| 4,725,010 A | 2/1988 | Lothamer | |
| 4,802,638 A | 2/1989 | Burger et al. | |
| 4,886,505 A | 12/1989 | Haynes et al. | |

(Continued)

FOREIGN PATENT DOCUMENTS

| WO | WO-00/74753 | 12/2000 |
|---|---|---|
| WO | WO-01/52935 | 7/2001 |

(Continued)

OTHER PUBLICATIONS

PCT Application No. PCT/US2007/072287, International Preliminary Report on Patentability and Written Opinion of the International Searching Authority mailed Jan. 15, 2009.

(Continued)

*Primary Examiner* — Navin Natnithithadha
(74) *Attorney, Agent, or Firm* — Jackson & Co., LLP

(57) ABSTRACT

Method and system for providing an integrated analyte monitoring system and on-body patch pump with multiple cannulas and a sensor combination is provided.

18 Claims, 3 Drawing Sheets

(56) References Cited

U.S. PATENT DOCUMENTS

| | | | | |
|---|---|---|---|---|
| 5,019,096 | A | 5/1991 | Fox, Jr. et al. | |
| 5,067,665 | A | 11/1991 | LoStracco et al. | |
| 5,097,834 | A * | 3/1992 | Skrabal | 600/366 |
| 5,109,577 | A | 5/1992 | Young | |
| 5,209,414 | A | 5/1993 | Clemens et al. | |
| 5,236,143 | A | 8/1993 | Dragon | |
| 5,237,993 | A | 8/1993 | Skrabal | |
| 5,250,023 | A | 10/1993 | Lee | |
| 5,266,359 | A | 11/1993 | Spielvogel | |
| 5,284,425 | A | 2/1994 | Holtermann et al. | |
| 5,344,411 | A | 9/1994 | Domb et al. | |
| 5,349,852 | A | 9/1994 | Kamen et al. | |
| 5,390,671 | A * | 2/1995 | Lord et al. | 600/347 |
| 5,437,656 | A | 8/1995 | Shikani et al. | |
| 5,451,424 | A | 9/1995 | Solomon et al. | |
| 5,515,390 | A | 5/1996 | Benton | |
| 5,526,844 | A | 6/1996 | Kamen et al. | |
| 5,533,389 | A | 7/1996 | Kamen et al. | |
| 5,558,640 | A | 9/1996 | Pfeiler | |
| 5,569,186 | A | 10/1996 | Lord et al. | |
| 5,593,852 | A | 1/1997 | Heller et al. | |
| 5,599,321 | A | 2/1997 | Conway et al. | |
| 5,601,435 | A | 2/1997 | Quy | |
| 5,662,904 | A | 9/1997 | Ferguson et al. | |
| 5,673,691 | A | 10/1997 | Abrams et al. | |
| 5,738,220 | A | 4/1998 | Geszler | |
| 5,822,715 | A | 10/1998 | Worthington et al. | |
| 5,899,855 | A | 5/1999 | Brown | |
| 5,918,603 | A | 7/1999 | Brown | |
| 5,925,021 | A | 7/1999 | Castellano et al. | |
| 5,954,643 | A * | 9/1999 | VanAntwerp et al. | 600/316 |
| 5,956,501 | A | 9/1999 | Brown | |
| 5,975,120 | A | 11/1999 | Novosel | |
| 5,988,545 | A | 11/1999 | King | |
| 6,083,248 | A | 7/2000 | Thompson | |
| 6,134,461 | A | 10/2000 | Say et al. | |
| 6,175,752 | B1 | 1/2001 | Say et al. | |
| 6,233,539 | B1 | 5/2001 | Brown | |
| 6,248,067 | B1 * | 6/2001 | Causey et al. | 600/365 |
| 6,254,586 | B1 * | 7/2001 | Mann et al. | 604/506 |
| 6,284,478 | B1 | 9/2001 | Heller et al. | |
| 6,379,301 | B1 | 4/2002 | Worthington et al. | |
| 6,427,088 | B1 | 7/2002 | Bowman, IV et al. | |
| 6,471,689 | B1 | 10/2002 | Joseph et al. | |
| 6,482,156 | B2 | 11/2002 | Iliff | |
| 6,484,045 | B1 * | 11/2002 | Holker et al. | 600/345 |
| 6,485,461 | B1 | 11/2002 | Mason et al. | |
| 6,498,043 | B1 | 12/2002 | Schulman et al. | |
| 6,554,798 | B1 | 4/2003 | Mann et al. | |
| 6,558,321 | B1 | 5/2003 | Burd et al. | |
| 6,562,001 | B2 | 5/2003 | Lebel et al. | |
| 6,564,105 | B2 | 5/2003 | Starkweather et al. | |
| 6,571,128 | B2 | 5/2003 | Lebel et al. | |
| 6,577,899 | B2 | 6/2003 | Lebel et al. | |
| 6,585,644 | B2 | 7/2003 | Lebel et al. | |
| 6,598,824 | B2 | 7/2003 | Schmidt | |
| 6,635,014 | B2 | 10/2003 | Starkweather et al. | |
| 6,641,562 | B1 | 11/2003 | Peterson | |
| 6,648,821 | B2 | 11/2003 | Lebel et al. | |
| 6,656,158 | B2 | 12/2003 | Mahoney et al. | |
| 6,656,159 | B2 | 12/2003 | Flaherty | |
| 6,659,948 | B2 | 12/2003 | Lebel et al. | |
| 6,668,196 | B1 | 12/2003 | Villegas et al. | |
| 6,669,669 | B2 | 12/2003 | Flaherty et al. | |
| 6,687,546 | B2 | 2/2004 | Lebel et al. | |
| 6,692,457 | B2 | 2/2004 | Flaherty | |
| 6,694,191 | B2 | 2/2004 | Starkweather et al. | |
| 6,699,218 | B2 | 3/2004 | Flaherty et al. | |
| 6,702,857 | B2 | 3/2004 | Brauker et al. | |
| 6,723,072 | B2 | 4/2004 | Flaherty et al. | |
| 6,733,446 | B2 | 5/2004 | Lebel et al. | |
| 6,736,797 | B1 | 5/2004 | Larsen et al. | |
| 6,740,059 | B2 | 5/2004 | Flaherty | |
| 6,740,075 | B2 | 5/2004 | Lebel et al. | |
| 6,741,877 | B1 | 5/2004 | Shults et al. | |
| 6,744,350 | B2 | 6/2004 | Blomquist | |
| 6,749,587 | B2 | 6/2004 | Flaherty | |
| 6,758,810 | B2 | 7/2004 | Lebel et al. | |
| 6,768,425 | B2 | 7/2004 | Flaherty et al. | |
| 6,789,195 | B1 | 9/2004 | Prihoda et al. | |
| 6,810,290 | B2 | 10/2004 | Lebel et al. | |
| 6,811,533 | B2 | 11/2004 | Lebel et al. | |
| 6,811,534 | B2 | 11/2004 | Bowman, IV et al. | |
| 6,813,519 | B2 | 11/2004 | Lebel et al. | |
| 6,830,558 | B2 | 12/2004 | Flaherty et al. | |
| 6,852,104 | B2 | 2/2005 | Blomquist | |
| 6,862,465 | B2 | 3/2005 | Shults et al. | |
| 6,873,268 | B2 | 3/2005 | Lebel et al. | |
| 6,882,940 | B2 | 4/2005 | Potts et al. | |
| 6,887,270 | B2 | 5/2005 | Miller et al. | |
| 6,896,666 | B2 * | 5/2005 | Kochamba | 604/141 |
| 6,902,207 | B2 | 6/2005 | Lickliter | |
| 6,916,159 | B2 | 7/2005 | Rush et al. | |
| 6,931,327 | B2 | 8/2005 | Goode, Jr. et al. | |
| 6,936,006 | B2 * | 8/2005 | Sabra | 600/300 |
| 6,946,446 | B2 | 9/2005 | Ma et al. | |
| 6,950,708 | B2 | 9/2005 | Bowman IV et al. | |
| 6,958,705 | B2 | 10/2005 | Lebel et al. | |
| 6,960,192 | B1 | 11/2005 | Flaherty et al. | |
| 6,974,437 | B2 | 12/2005 | Lebel et al. | |
| 7,003,336 | B2 * | 2/2006 | Holker et al. | 600/316 |
| 7,018,360 | B2 | 3/2006 | Flaherty et al. | |
| 7,024,245 | B2 | 4/2006 | Lebel et al. | |
| 7,029,455 | B2 | 4/2006 | Flaherty | |
| 7,034,677 | B2 | 4/2006 | Steinthal et al. | |
| 7,052,251 | B2 | 5/2006 | Nason et al. | |
| 7,052,472 | B1 | 5/2006 | Miller et al. | |
| 7,066,922 | B2 * | 6/2006 | Angel et al. | 604/500 |
| 7,074,307 | B2 | 7/2006 | Simpson et al. | |
| 7,077,328 | B2 | 7/2006 | Krishnaswamy et al. | |
| 7,079,977 | B2 | 7/2006 | Osorio et al. | |
| 7,081,195 | B2 | 7/2006 | Simpson et al. | |
| 7,108,778 | B2 | 9/2006 | Simpson et al. | |
| 7,110,803 | B2 | 9/2006 | Shults et al. | |
| 7,113,821 | B1 * | 9/2006 | Sun et al. | 604/21 |
| 7,133,717 | B2 * | 11/2006 | Coston et al. | 604/20 |
| 7,134,999 | B2 | 11/2006 | Brauker et al. | |
| 7,136,689 | B2 | 11/2006 | Shults et al. | |
| 7,137,964 | B2 | 11/2006 | Flaherty | |
| 7,144,384 | B2 | 12/2006 | Gorman et al. | |
| 7,155,112 | B2 | 12/2006 | Uno et al. | |
| 7,167,818 | B2 | 1/2007 | Brown | |
| 7,171,274 | B2 | 1/2007 | Starkweather et al. | |
| 7,171,312 | B2 | 1/2007 | Steinthal et al. | |
| 7,192,450 | B2 | 3/2007 | Brauker et al. | |
| 7,226,278 | B2 | 6/2007 | Nason et al. | |
| 7,226,978 | B2 | 6/2007 | Tapsak et al. | |
| 7,229,042 | B2 | 6/2007 | Thebault et al. | |
| 7,267,665 | B2 * | 9/2007 | Steil et al. | 604/131 |
| 7,276,029 | B2 | 10/2007 | Goode, Jr. et al. | |
| 7,303,549 | B2 | 12/2007 | Flaherty et al. | |
| 7,310,544 | B2 | 12/2007 | Brister et al. | |
| 7,364,568 | B2 * | 4/2008 | Angel et al. | 604/173 |
| 7,364,592 | B2 | 4/2008 | Carr-Brendel et al. | |
| 7,366,556 | B2 | 4/2008 | Brister et al. | |
| 7,379,765 | B2 | 5/2008 | Petisce et al. | |
| 7,424,318 | B2 | 9/2008 | Brister et al. | |
| 7,429,258 | B2 * | 9/2008 | Angel et al. | 604/173 |
| 7,460,898 | B2 | 12/2008 | Brister et al. | |
| 7,467,003 | B2 | 12/2008 | Brister et al. | |
| 7,471,972 | B2 | 12/2008 | Rhodes et al. | |
| 7,483,736 | B2 * | 1/2009 | Marchitto et al. | 604/20 |
| 7,494,465 | B2 | 2/2009 | Brister et al. | |
| 7,497,827 | B2 | 3/2009 | Brister et al. | |
| 7,519,408 | B2 | 4/2009 | Rasdal et al. | |
| 7,583,990 | B2 | 9/2009 | Goode, Jr. et al. | |
| 7,591,801 | B2 | 9/2009 | Brauker et al. | |
| 7,599,726 | B2 | 10/2009 | Goode, Jr. et al. | |
| 7,613,491 | B2 | 11/2009 | Boock et al. | |
| 7,615,007 | B2 | 11/2009 | Shults et al. | |
| 7,632,228 | B2 | 12/2009 | Brauker et al. | |
| 7,637,868 | B2 | 12/2009 | Saint et al. | |
| 7,640,048 | B2 | 12/2009 | Dobbles et al. | |
| 7,645,263 | B2 * | 1/2010 | Angel et al. | 604/116 |

| Patent/Publication | Date | Inventors |
|---|---|---|
| 7,651,596 B2 | 1/2010 | Petisce et al. |
| 7,654,956 B2 | 2/2010 | Brister et al. |
| 7,657,297 B2 | 2/2010 | Simpson et al. |
| 7,711,402 B2 | 5/2010 | Shults et al. |
| 7,713,574 B2 | 5/2010 | Brister et al. |
| 7,715,893 B2 | 5/2010 | Kamath et al. |
| 2002/0016719 A1 | 2/2002 | Nemeth et al. |
| 2002/0019612 A1 | 2/2002 | Watanabe et al. |
| 2002/0106709 A1 | 8/2002 | Potts et al. |
| 2002/0107476 A1 | 8/2002 | Mann et al. |
| 2002/0147135 A1 | 10/2002 | Schnell |
| 2002/0169439 A1 | 11/2002 | Flaherty et al. |
| 2002/0193679 A1 | 12/2002 | Malave et al. |
| 2003/0023317 A1 | 1/2003 | Brauker et al. |
| 2003/0032874 A1 | 2/2003 | Rhodes et al. |
| 2003/0055380 A1 | 3/2003 | Flaherty et al. |
| 2003/0060753 A1 | 3/2003 | Starkweather et al. |
| 2003/0065308 A1 | 4/2003 | Lebel et al. |
| 2003/0069541 A1 | 4/2003 | Gillis et al. |
| 2003/0073414 A1 | 4/2003 | Capps |
| 2003/0114836 A1 | 6/2003 | Estes et al. |
| 2003/0122021 A1 | 7/2003 | McConnell et al. |
| 2003/0130616 A1 | 7/2003 | Steil et al. |
| 2003/0144362 A1 | 7/2003 | Utterberg et al. |
| 2003/0167035 A1 | 9/2003 | Flaherty et al. |
| 2003/0175323 A1 | 9/2003 | Utterberg et al. |
| 2003/0176933 A1 | 9/2003 | Lebel et al. |
| 2003/0212379 A1 | 11/2003 | Bylund et al. |
| 2003/0217966 A1 | 11/2003 | Tapsak et al. |
| 2003/0225361 A1 | 12/2003 | Sabra |
| 2004/0010207 A1 | 1/2004 | Flaherty et al. |
| 2004/0011671 A1 | 1/2004 | Shults et al. |
| 2004/0015131 A1 | 1/2004 | Flaherty et al. |
| 2004/0041749 A1 | 3/2004 | Dixon |
| 2004/0045879 A1 | 3/2004 | Shults et al. |
| 2004/0064088 A1 | 4/2004 | Gorman et al. |
| 2004/0064096 A1 | 4/2004 | Flaherty et al. |
| 2004/0122530 A1 | 6/2004 | Hansen et al. |
| 2004/0133390 A1 | 7/2004 | Osorio et al. |
| 2004/0135684 A1 | 7/2004 | Steinthal et al. |
| 2004/0153032 A1 | 8/2004 | Garribotto et al. |
| 2004/0155770 A1 | 8/2004 | Nelson et al. |
| 2004/0162521 A1* | 8/2004 | Bengtsson ................ 604/136 |
| 2004/0167464 A1 | 8/2004 | Ireland et al. |
| 2004/0186362 A1 | 9/2004 | Brauker et al. |
| 2004/0193025 A1 | 9/2004 | Steil et al. |
| 2004/0193090 A1 | 9/2004 | Lebel et al. |
| 2004/0199059 A1 | 10/2004 | Brauker et al. |
| 2004/0210180 A1 | 10/2004 | Altman |
| 2004/0210208 A1 | 10/2004 | Paul et al. |
| 2004/0225338 A1 | 11/2004 | Lebel et al. |
| 2004/0254433 A1* | 12/2004 | Bandis et al. ............... 600/347 |
| 2005/0004439 A1 | 1/2005 | Shin et al. |
| 2005/0010269 A1 | 1/2005 | Lebel et al. |
| 2005/0027180 A1 | 2/2005 | Goode et al. |
| 2005/0031689 A1 | 2/2005 | Shults et al. |
| 2005/0038332 A1 | 2/2005 | Saidara et al. |
| 2005/0038674 A1 | 2/2005 | Braig et al. |
| 2005/0043598 A1 | 2/2005 | Goode, Jr. et al. |
| 2005/0065464 A1 | 3/2005 | Talbot et al. |
| 2005/0090607 A1 | 4/2005 | Tapsak et al. |
| 2005/0112169 A1 | 5/2005 | Brauker et al. |
| 2005/0113653 A1 | 5/2005 | Fox et al. |
| 2005/0119540 A1 | 6/2005 | Potts et al. |
| 2005/0143635 A1 | 6/2005 | Kamath et al. |
| 2005/0171512 A1 | 8/2005 | Flaherty |
| 2005/0176136 A1 | 8/2005 | Burd et al. |
| 2005/0181010 A1 | 8/2005 | Hunter et al. |
| 2005/0182306 A1 | 8/2005 | Sloan |
| 2005/0182358 A1 | 8/2005 | Veit et al. |
| 2005/0182366 A1 | 8/2005 | Vogt et al. |
| 2005/0187720 A1 | 8/2005 | Goode et al. |
| 2005/0192557 A1 | 9/2005 | Brauker et al. |
| 2005/0195930 A1 | 9/2005 | Spital et al. |
| 2005/0203461 A1 | 9/2005 | Flaherty et al. |
| 2005/0238507 A1 | 10/2005 | DiIanni et al. |
| 2005/0245795 A1 | 11/2005 | Goode et al. |
| 2005/0245799 A1 | 11/2005 | Brauker et al. |
| 2005/0261667 A1 | 11/2005 | Crank et al. |
| 2006/0001551 A1 | 1/2006 | Kraft et al. |
| 2006/0004603 A1 | 1/2006 | Peterka et al. |
| 2006/0015020 A1 | 1/2006 | Neale et al. |
| 2006/0016700 A1 | 1/2006 | Brister et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0041229 A1 | 2/2006 | Garibotto et al. |
| 2006/0065772 A1 | 3/2006 | Grant et al. |
| 2006/0095020 A1 | 5/2006 | Casas et al. |
| 2006/0154642 A1 | 7/2006 | Scannell |
| 2006/0173406 A1 | 8/2006 | Hayes et al. |
| 2006/0173444 A1 | 8/2006 | Choy et al. |
| 2006/0173712 A1 | 8/2006 | Joubert |
| 2006/0178633 A1 | 8/2006 | Garibotto et al. |
| 2006/0222566 A1 | 10/2006 | Brauker et al. |
| 2006/0224141 A1 | 10/2006 | Rush et al. |
| 2006/0282290 A1 | 12/2006 | Flaherty et al. |
| 2006/0293577 A1 | 12/2006 | Morrison et al. |
| 2007/0016381 A1 | 1/2007 | Kamath et al. |
| 2007/0060869 A1 | 3/2007 | Tolle et al. |
| 2007/0060870 A1 | 3/2007 | Tolle et al. |
| 2007/0060871 A1 | 3/2007 | Istoc et al. |
| 2007/0078818 A1 | 4/2007 | Zivitz et al. |
| 2007/0093786 A1 | 4/2007 | Goldsmith et al. |
| 2007/0100222 A1 | 5/2007 | Mastrototaro et al. |
| 2007/0118405 A1 | 5/2007 | Campbell et al. |
| 2007/0128682 A1 | 6/2007 | Rosman et al. |
| 2007/0129621 A1 | 6/2007 | Kellogg et al. |
| 2007/0163880 A1 | 7/2007 | Woo et al. |
| 2007/0191702 A1 | 8/2007 | Yodfat et al. |
| 2007/0203966 A1 | 8/2007 | Brauker et al. |
| 2007/0208246 A1 | 9/2007 | Brauker et al. |
| 2007/0213657 A1 | 9/2007 | Jennewine et al. |
| 2007/0219480 A1 | 9/2007 | Kamen et al. |
| 2007/0219597 A1 | 9/2007 | Kamen et al. |
| 2007/0235331 A1 | 10/2007 | Simpson et al. |
| 2007/0255114 A1 | 11/2007 | Ackermann et al. |
| 2007/0299409 A1 | 12/2007 | Whitbourne et al. |
| 2008/0004515 A1* | 1/2008 | Jennewine ................ 600/345 |
| 2008/0004601 A1 | 1/2008 | Jennewine et al. |
| 2008/0018480 A1 | 1/2008 | Sham |
| 2008/0021666 A1 | 1/2008 | Goode et al. |
| 2008/0033254 A1 | 2/2008 | Kamath et al. |
| 2008/0045824 A1 | 2/2008 | Tapsak et al. |
| 2008/0071156 A1 | 3/2008 | Brister et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0093447 A1 | 4/2008 | Johnson et al. |
| 2008/0108942 A1 | 5/2008 | Brister et al. |
| 2008/0183061 A1 | 7/2008 | Goode, Jr. et al. |
| 2008/0183399 A1 | 7/2008 | Goode, Jr. et al. |
| 2008/0188731 A1 | 8/2008 | Brister et al. |
| 2008/0189051 A1 | 8/2008 | Goode, Jr. et al. |
| 2008/0194935 A1 | 8/2008 | Brister et al. |
| 2008/0194936 A1 | 8/2008 | Goode, Jr. et al. |
| 2008/0194937 A1 | 8/2008 | Goode, Jr. et al. |
| 2008/0194938 A1 | 8/2008 | Brister et al. |
| 2008/0195232 A1 | 8/2008 | Carr-Brendel et al. |
| 2008/0195967 A1 | 8/2008 | Goode, Jr. et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0208025 A1 | 8/2008 | Shults et al. |

| | | |
|---|---|---|
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0228055 A1 | 9/2008 | Sher |
| 2008/0242961 A1 | 10/2008 | Brister et al. |
| 2008/0262469 A1 | 10/2008 | Brister et al. |
| 2008/0269687 A1 | 10/2008 | Chong et al. |
| 2008/0275313 A1 | 11/2008 | Brister et al. |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0296155 A1 | 12/2008 | Shults et al. |
| 2008/0306368 A1 | 12/2008 | Goode, Jr. et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2009/0012379 A1 | 1/2009 | Goode, Jr. et al. |
| 2009/0018424 A1 | 1/2009 | Kamath et al. |
| 2009/0030294 A1 | 1/2009 | Petisce et al. |
| 2009/0036758 A1 | 2/2009 | Brauker et al. |
| 2009/0036763 A1 | 2/2009 | Brauker et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0062633 A1 | 3/2009 | Brauker et al. |
| 2009/0062635 A1 | 3/2009 | Brauker et al. |
| 2009/0069650 A1 * | 3/2009 | Jennewine .................. 600/309 |
| 2009/0076356 A1 | 3/2009 | Simpson et al. |
| 2009/0076360 A1 | 3/2009 | Brister et al. |
| 2009/0076361 A1 | 3/2009 | Kamath et al. |
| 2009/0099436 A1 | 4/2009 | Brister et al. |
| 2009/0124877 A1 | 5/2009 | Brauker et al. |
| 2009/0124878 A1 | 5/2009 | Goode, Jr. et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0178459 A1 | 7/2009 | Li et al. |
| 2009/0182217 A1 | 7/2009 | Li et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0203981 A1 | 8/2009 | Brauker et al. |
| 2009/0204341 A1 | 8/2009 | Brauker et al. |
| 2009/0216103 A1 | 8/2009 | Brister et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0287073 A1 | 11/2009 | Boock et al. |
| 2009/0287074 A1 | 11/2009 | Shults et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049024 A1 | 2/2010 | Saint et al. |
| 2010/0063373 A1 | 3/2010 | Kamath et al. |
| 2010/0076283 A1 | 3/2010 | Simpson et al. |
| 2010/0081908 A1 | 4/2010 | Dobbles et al. |
| 2010/0081910 A1 | 4/2010 | Brister et al. |
| 2010/0087724 A1 | 4/2010 | Brauker et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0119693 A1 | 5/2010 | Tapsak et al. |
| 2010/0121169 A1 | 5/2010 | Petisce et al. |
| 2010/0292634 A1 | 11/2010 | Kircher et al. |

FOREIGN PATENT DOCUMENTS

| | | |
|---|---|---|
| WO | WO-01/54753 | 8/2001 |
| WO | WO-02/39086 | 5/2002 |
| WO | WO-03/006091 | 1/2003 |
| WO | WO-03/090509 | 4/2003 |
| WO | WO-03/053503 | 7/2003 |
| WO | WO-03/071930 | 9/2003 |
| WO | WO-03/103763 | 12/2003 |
| WO | WO-2006/037109 | 4/2006 |
| WO | WO-2007/101260 | 9/2007 |
| WO | WO-2008/003003 | 1/2008 |
| WO | WO-2008/005780 | 1/2008 |
| WO | WO-2008/086541 | 7/2008 |

OTHER PUBLICATIONS

PCT Application No. PCT/US2007/072287, International Search Report and Written Opinion of the International Searching Authority mailed Jul. 25, 2008.
U.S. Appl. No. 11/428,299, Advisory Action mailed Aug. 14, 2009.
U.S. Appl. No. 11/428,299, Office Action mailed Apr. 6, 2010.
U.S. Appl. No. 11/428,299, Office Action mailed Jul. 31, 2008.
U.S. Appl. No. 11/428,299, Office Action mailed Mar. 17, 2009.
U.S. Appl. No. 11/428,299, Office Action mailed Nov. 7, 2007.
U.S. Appl. No. 11/428,299, Office Action mailed Oct. 7, 2009.
U.S. Appl. No. 11/428,299, Advisory Action mailed Dec. 21, 2010.
U.S. Appl. No. 11/428,299, Office Action mailed Sep. 13, 2010.

* cited by examiner

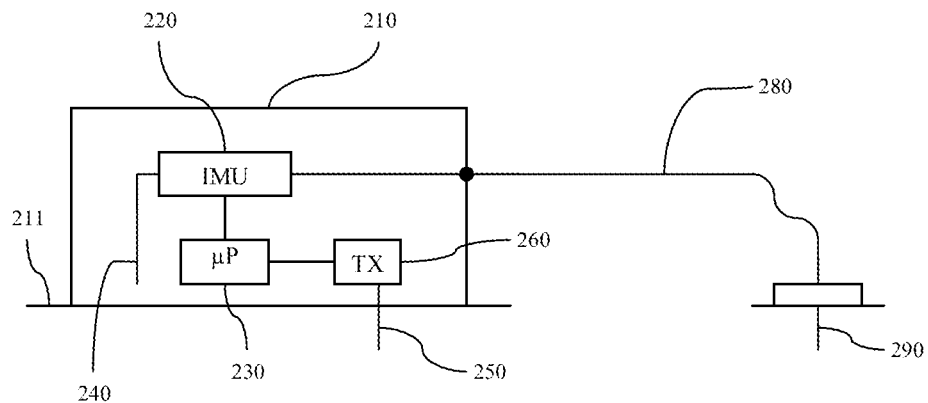
FIGURE 3
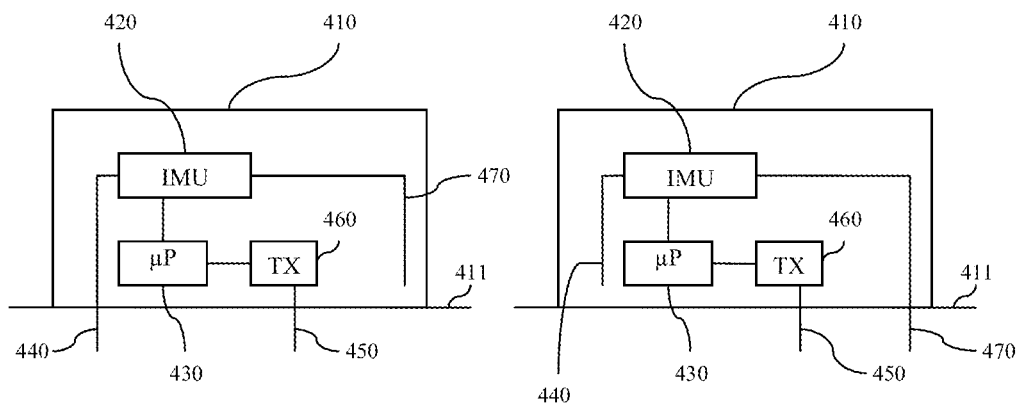
FIGURE 4A
FIGURE 4B

INTEGRATED ANALYTE SENSOR AND INFUSION DEVICE AND METHODS THEREFOR

RELATED APPLICATIONS

This application is a divisional of pending U.S. patent application Ser. No. 11/428,299 filed Jun. 30, 2006, entitled "Integrated Analyte Sensor And Infusion Device And Methods Therefor," the disclosure of which is incorporated herein by reference for all purposes.

BACKGROUND

Diabetic patients periodically administer insulin to sustain their physiological conditions. Typically, these patients administer doses of either fast acting or slow acting insulin using needle type syringes, for example, prior to meals, and/or at a suitable time during the course of each day contemporaneously with the blood glucose level testing using fingerstick testing, for example. If insulin is not suitably administered, the diabetic patients risk serious if not fatal damage to the body.

Continued development and improvement in the external infusion pump therapy in recent years have drawn much appeal to the diabetic patients for, among others, improved management of diabetes by better regulating and controlling the intake of insulin. Typically, the patient inserts a cannula which is connected as infusion tubing attached to an external pump, and insulin is administered based on preprogrammed basal profiles. Moreover, the external infusion devices presently available include computational capability to determined suitable bolus doses such as carbohydrate bolus and correction bolus, for example, to be administered in conjunction with the infusion device executing the patient's basal profile.

Typically, the infusion site where the cannula is positioned under the skin layer of the patient experiences tissue or skin trauma. Thus, the infusion site is typically changed with each change of the infusion set, for example, every three days or so. Furthermore, the infusion site may also be prone to infection and other adverse consequences as a result of the transcutaneous placement of the cannula for insulin delivery.

In addition, current development in analyte monitoring typically uses a transcutaneously positioned biosensor which is in fluid contact with the patient's analyte to monitor, for example, analyte levels of the patient. Given that the useful life of the biosensor may not coincide with the typical 3 or so day usage of an infusion set, a patient using an infusion device and also using an analyte monitoring system must periodically replace the cannula for the infusion system, and the biosensor for the analyte monitoring system, and which may be at different times during the course of infusion therapy and analyte monitoring.

SUMMARY OF THE INVENTION

In view of the foregoing, in accordance with the various embodiments of the present invention, there is provided an integrated analyte monitoring system and on-body patch pump with multiple cannulas and a sensor combination. In particular, within the scope of the present invention, there are provided methods and system for deploying multiple infusion cannulas for use with an extended analyte sensor (for example, a 7 day sensor).

These and other objects, features and advantages of the present invention will become more fully apparent from the following detailed description of the embodiments, the appended claims and the accompanying drawings.

BRIEF DESCRIPTION OF THE DRAWINGS

FIG. 3 illustrates a combined patch pump system integrated with the second cannula during the second part of the sensor life in accordance with one embodiment of the present invention;

FIGS. 4A and 4B illustrate multiple cannulas integrated with an extended use analyte sensor in a patch pump configuration in accordance with another embodiment of the present invention.

DETAILED DESCRIPTION

As described below, within the scope of the present invention, there are provided methods and systems for integrating therapeutic fluid infusion cannula for use with an on-body patch pump and an analyte sensor configured for continuous monitoring of a patient's analyte. In particular, within the scope of the present invention, there is provided an integrated multiple infusion cannulas with analyte sensors for continuous monitoring and infusion for approximately seven days of continuous use.

Figure 1:
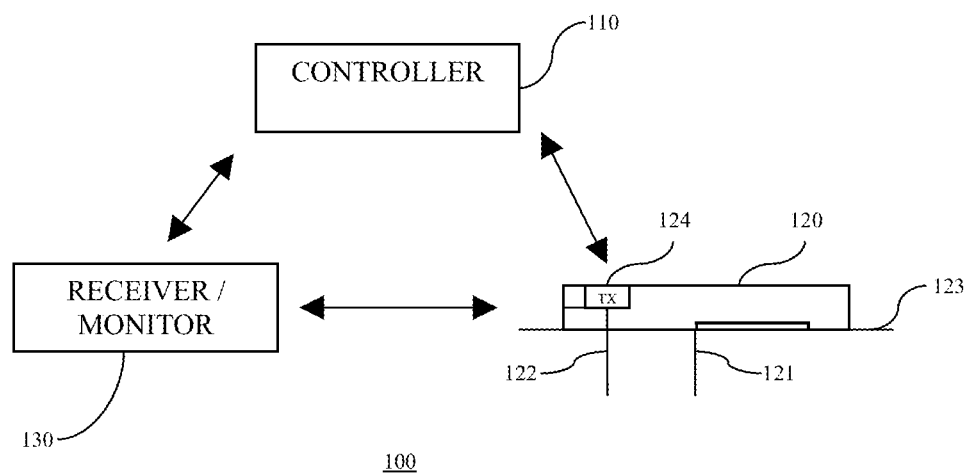
FIG. 1 is a block diagram illustrating an overall therapy management system for practicing one embodiment of the present invention.

FIG. 1 is a block diagram illustrating an overall therapy management system for practicing one embodiment of the present invention. Referring to FIG. 1, the therapy management system 100 includes a controller 110 configured for bi-directional wireless communication with an on-body patch pump 120. In one embodiment, the controller 110 is configured to control the operation of the patch pump 120 based on, for example, preprogrammed delivery profiles for infusion of therapeutic agent, such as, including but not limited to insulin. In one aspect, the controller 110 includes one or more user input unit, and one or more user output unit for user directed programming of the patch pump 120 using the controller 110, and further, to provide visual, auditory, and/or vibratory output signals for communicating with the user.

Referring back to FIG. 1, the patch pump 120 in one embodiment is provided with an adhesive layer 123 which is configured to adhere on the skin of a patient during use. The patch pump 120 includes a cannula 121 for establishing a fluid path between a reservoir (not shown) containing the therapeutic fluid for delivery and the infusion site of the patient. Also shown in the Figure is a sensor 122. As shown in FIG. 1, a portion of the cannula 121 and the sensor 122 are positioned under the skin of the patient, and thus, at least a portion of each are configured to extend from the lower surface of the patch pump 120 through the skin layer of the patient.

In one embodiment, the sensor 122 includes an analyte sensor which is configured to establish fluid contact with the interstitial fluid of the patient so as to detect the analyte level, such as glucose level, of the patient. That is, the transmitter unit 124 may be configured to receive one or more signals from the analyte sensor 122 corresponding to the detected analyte levels of the patient, and to transmit the information corresponding to the detected analyte levels to the receiver/monitor 130 and/or the controller 110. In particular, over a communication link such as an RF wireless communication link, the transmitter unit 124 may be configured to transmit data associated with the detected analyte levels periodically, and/or intermittently and repeatedly to one or more other devices such as controller 110 and/or the receiver/monitor 130 for further data processing and analysis.

Referring back to FIG. 1, in one embodiment, the one or more of the controller 110 and the receiver/monitor 130 may include a strip port configured to receive a test strip for capillary blood glucose testing. In one aspect, the glucose level measured using the test strip may in addition, be configured to provide periodic calibration of the sensor 122 to assure and improve the accuracy of the analyte levels detected by the analyte sensor 122.

Referring again to FIG. 1, the analyte sensor 122 may include, but is not limited to, short term subcutaneous analyte sensors or transdermal analyte sensors, for example, which are configured to detect analyte levels of a patient over a predetermined time period, and after which, a replacement of the sensors is necessary. Additional analytes that may be monitored, determined or detected by the analyte monitoring system include, for example, acetyl choline, amylase, amyln, bilirubin, cholesterol, chorionic gonadotropin, creatine kinase (e.g., CK-MB), creatine, DNA, fructosamine, glucose, glutamine, growth hormones, hormones, ketones, lactate, measures for oxidative stress (such as 8-iso PGF2gamma), peroxide, prostate-specific antigen, prothrombin, RNA, thyroid stimulating hormone, and troponin. The concentration of drugs, such as, for example, antibiotics (e.g., gentamicin, vancomycin, and the like), biguanides, digitoxin, digoxin, drugs of abuse, GLP-1, insulin, PPAR agonists, sulfonylureas, theophylline, thiazolidinediones, and warfarin, may also be determined.

Referring yet again to FIG. 1, both the cannula 121 and the sensor 122 may be transcutaneously positioned under the skin layer of the patient using an insertion device (not shown) that includes a sharp penetrating member such as an insertion needle. Alternatively, the sensor 122 and the cannula 121 may be configured with sufficient rigidity to pierce through the skin of the patient without additional piercing guides such as the sharp penetrating member of the insertion device.

Further, the transmitter unit 124 in one embodiment is configured to maintain electrical communication with the sensor 122 such that the detected analyte levels from the sensor 122 may be transmitted by the transmitter unit 124 to the controller 110. In this manner, the controller 110 may be configured to communicate with the transmitter unit 124 so as to provide analyte monitoring functions.

Alternatively or in addition to the controller 110, there may be provided a receiver/monitor unit 130 which is configured to communicate with the transmitter unit 124 to receive the detected analyte levels for further processing. In one aspect, the patch pump 120 control functions and the analyte monitoring functions may be incorporated in the controller 110 such that the patient need only carry one device. In addition, the receiver/monitor unit 130 in one embodiment may include for example, a desktop computer terminal, a data communication enabled kiosk, a laptop computer, a handheld computing device such as a personal digital assistant (PDAs), or a data communication enabled mobile telephone.

Similar to the controller 110 discussed above, the receiver/monitor unit 130 may include a user interface unit which may include a display unit and/or an audio output unit such as, for example, a speaker, and/or any other suitable user interface mechanism for displaying or informing the user of such devices.

In one embodiment, both the controller 110 and the receive/monitor 130 are configured with a substantially compact housing and sized such that the devices may be easily and comfortably held in the patient's hand, worn on the patient's clothing, or placed inside a pocket of the patient's clothing without much discomfort. In addition, the patch pump 120 may be configured with a substantially compact housing and sized such that the patient experiences minimal discomfort during the seven or more days of continuous on-body use.

Figures 2A, 2B:
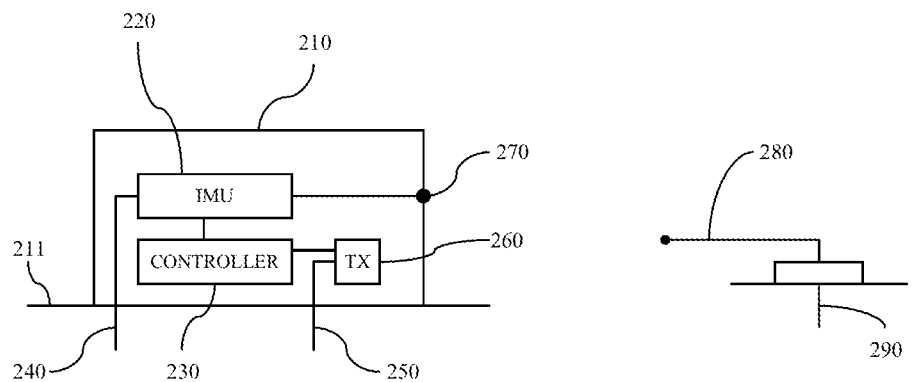
FIGS. 2A and 2B illustrate multiple cannulas integrated with an extended use analyte sensor in a patch pump configuration in accordance with one embodiment of the present invention.

FIGS. 2A and 2B illustrate multiple cannulas integrated with an extended use analyte sensor in a patch pump configuration in accordance with one embodiment of the present invention. Referring to FIG. 2A, patch pump 210 in one embodiment includes a controller 230 (e.g., a microprocessor) operatively coupled to an infusion management unit (IMU) 220 which includes, among others, a reservoir (not shown) for retaining a therapeutic agent such as insulin for delivery to the patient. Within the scope of the present invention, the infusion management unit (IMU) 220 may include other components such as power supply (e.g., battery), and/or fluid path management section which, in one embodiment, may be configured to connect the a cannula 240 to the reservoir for therapeutic agent delivery to the patient, and further, to control the placement or positioning of the first cannula 240, and subsequent retraction of the first cannula 240 upon reaching the end of its useful life cycle.

Moreover, in one embodiment, the infusion management unit (IMU) 220 may include a transceiver (not shown) for bi-directional communication with one or more of the controller 110 and the receiver/monitor 130. In one embodiment, the transceiver may be configured to receive infusion related commands or instructions from the one or more of the controller 110 and the receiver/monitor 130, and further, to transmit one or more information associated with the fluid flow information or the operating condition of the patch pump 120.

Referring back to FIG. 2A, the infusion management unit (IMU) 220 in one embodiment is connected to a port 270 provided substantially at the housing of the patch pump 210. In one aspect, the infusion management unit (IMU) 220 is configured to maintain a fluid path to the port 270. In one embodiment, the port 270 may include a self-sealing septum which is substantially configured to be water proof. In accordance with an alternate embodiment, the port 270 may include a uni-directional connector for mating with an infusion tubing 280 to establish fluid path between the infusion management unit 220 and a second cannula 290 as shown in FIG. 2B. That is, in one embodiment, the infusion management unit (IMU) 220 may be configured to manage the infusion of the therapeutic agent such that the first cannula 240 transcutaneously positioned at the first infusion site is used for a predetermined time period (for example, approximately three to four days), and thereafter, retract the first cannula 240 from the first infusion site (and retained within the housing of the patch pump 210), while connecting the infusion tubing 280 to the port 270 establishes a fluid path to the second cannula 290 to infuse the therapeutic agent to the patient in a continuous manner.

Referring yet again to FIG. 2A, also provided in the patch pump 210 is a sensor 250 such as, for example, an analyte sensor, at least a portion of which is transcutaneously positioned under the skin layer of the patient. As shown, the sensor 250 is operatively coupled to a transmitter unit 260 which is configured to communicate with, for example, the controller 110 (FIG. 1) and/or the receiver/monitor 130 (FIG.

1). In one aspect, the sensor 250 is configured for approximately seven or more days of use. As such, it is desirable to change the infusion site of the therapeutic agent delivery at approximately mid point in the usage life of the sensor 250 (i.e., after approximately three or four days of use).

Accordingly, in accordance with one embodiment of the present invention, the first cannula 240 is configured for transcutaneous delivery of the therapeutic agent at the first infusion site for the initial time period of approximately three or four days. Thereafter, the first cannula 240 is retracted from the infusion site under the control and operation of one or more of the controller 230 and the infusion management unit 220, and in one embodiment, wholly retained within the housing of the patch pump 210. Prior to the retraction of the first cannula 240, the infusion tubing 280 connected to the second cannula 290 is coupled to the port 270 to establish fluid contact with the infusion management unit (IMU) 220. This is shown in FIG. 3.

The tubing 280 may be either pre-primed or is primed by the controller 230 and/or the infusion management unit (IMU) 220. In addition, the tip of the tubing 280 for mating or connection to the port 270 may be configured to engage with the port 270 so as to establish a water tight seal. Further, the second cannula 290 is transcutaneously positioned at the second infusion site (which is different from the first infusion site on the patient) for delivery of the therapeutic agent.

In one embodiment, the insertion process of the second cannula 290 may be automated using an insertion device such as an insertion gun that is configured to couple to the second cannula 290 (for example, the insertion needle coupled to the second cannula 290) and which includes a spring bias driven insertion mechanism. Alternatively, the insertion process may be primarily manual whereby the patient manually inserts the second cannula at the desired second infusion site.

In this manner, in one embodiment, the patch pump 210 may be configured for operation for approximately seven or more days for therapeutic agent delivery, and further, integrated with a continuous monitoring system wherein the sensor 250 is configured to continuously monitor the analyte level of the patient during the seven or more days of use without interruption. The monitored analyte levels as well as the therapeutic agent delivery associated information are communicated to the controller 110 (FIG. 1) and/or the receiver/monitor 130 by, for example, the transmitter unit 260. Furthermore, by changing the infusion site for the therapeutic agent delivery to the patient, potential for skin irritation and/or damage to patient's tissue at the infusion site by the cannula and/or the therapeutic agent may be minimized.

FIGS. 4A and 4B illustrate multiple cannulas integrated with an extended use analyte sensor in a patch pump configuration in accordance with another embodiment of the present invention. Referring to FIG. 4A, patch pump 410 in one embodiment includes a first cannula 440 and a second cannula 470 disposed therein. Also shown in the Figure is the infusion management unit (IMU) 420 which is operatively coupled to the first cannula 440 and the second cannula 470.

Further, a controller 430 is operatively coupled to the infusion management unit (IMU) 420 and to a transmitter unit 460. Similar to the controller 230 discussed above in conjunction with FIGS. 2A-2B and 3, the controller 430 in one embodiment is configured to control the operating functions of the infusion management unit (IMU) 420 and the transmitter unit 460, for managing therapeutic agent delivery via the respective first and second cannulas 440, 470, and for managing the data transmission of the transmitter unit 460 that is configured to receive one or more analyte associated signals from a sensor 450.

Referring back to FIG. 4A, in one embodiment, the initial transcutaneous placement of the sensor 450 and the first cannula 440 is performed substantially simultaneously (or near simultaneously). Thereafter, when a predetermined time period has lapsed, the first cannula 440 is configured to be withdrawn from the infusion site, while the second cannula (pre-deployed) is transcutaneously inserted into the patient. An adhesive patch 411 is configured to substantially fixedly retain the patch pump 410 on the adhered portion of the patient's skin during the entire duration of the patch pump 410 usage (for example, seven or more days).

Referring now to FIG. 4B, it can be seen that the first cannula 440 in one embodiment is withdrawn from the first infusion site, and substantially and entirely retained within the housing of the patch pump 410, while the second cannula 470 is transcutaneously positioned at the second infusion site. As discussed above, the infusion management unit (IMU) 420 in one embodiment includes a reservoir containing the therapeutic agent, and to establish the appropriate fluid communication with the first and second cannulas 440, 470. Optionally, the controller 430 may be configured to control the operation of the infusion management unit (IMU) 420 so as to provide continuous and uninterrupted delivery of the therapeutic agent to the patient during the duration in which the sensor 450 is detecting the analyte levels of the patient.

In one embodiment, the controller 110 (FIG. 1) and/or the receiver/monitor 130 may be configured to substantially control the programming of the patch pump 410 such that the operation of the infusion management unit (IMU) 420 and the controller 430 of the patch pump 410 are configured to receive the commands or instructions from the controller 110 and/or the receiver/monitor 130 to execute the appropriate functions. Examples of such functions include, but are not limited to, the delivery of programmed basal profiles, delivery of carbohydrate bolus dosage, implementing a temporary basal modification, insertion and/or retraction of the first cannula 440, and the insertion and/or retraction of the second cannula 470.

In a further embodiment, a mounting base (not shown) may be provided which includes the adhesive layer 411 there under, and which may be configured to guide the insertion of the first cannula 440 and the sensor 450. Further, the first cannula 440 and the sensor 450 may be transcutaneously positioned prior to the placement or positioning of the patch pump 410 on the patient's skin. In this configuration, the first cannula 440 and the sensor 450 may not be initially retained within the housing of the patch pump 410. Rather, an insertion device may be used to separately insert the first cannula 440 and the sensor 450. Thereafter, the patch pump 410 may be configured to couple to the transcutaneously positioned first cannula 440 and the sensor 450 such that the first cannula establishes fluid contact with the infusion management unit (IMU) 420, and the sensor 450 is in electrical contact with the transmitter unit 460.

Figure 5A:
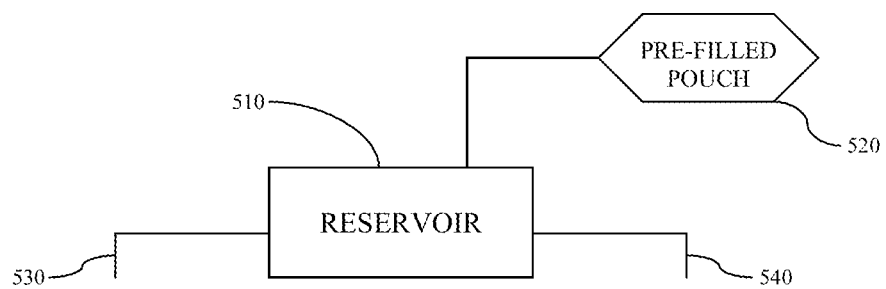
FIGS. 5A and 5B illustrate alternate embodiments showing infusion fluid provision in accordance with one embodiment of the present invention.
Figure 5B:
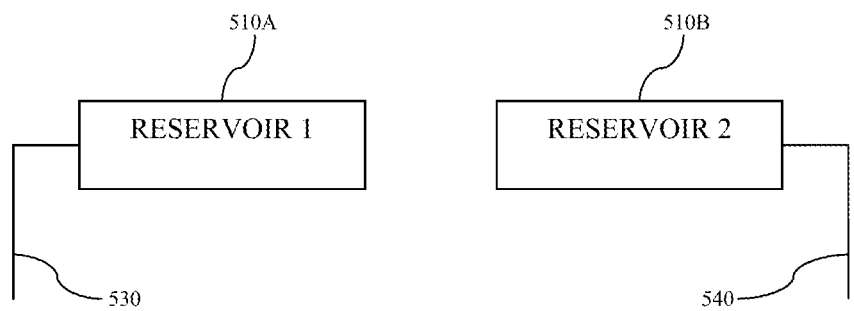

FIGS. 5A and 5B illustrate alternate embodiments showing infusion fluid provision in accordance with one embodiment of the present invention. Referring to FIG. 5A, it can be seen that a first cannula 530 and a second cannula 540 are coupled to the reservoir 510, while the reservoir 510 is further coupled to a pre-filled pouch 520. In one embodiment, the infusion management unit (IMU) 220 or 420 may be configured to include the first and second cannulas 530, 540, the reservoir 510 and the pre-filled pouch 520. The pre-filled pouch is configured to hold a therapeutic agent such as insulin to replenish the reservoir during the usage life of the patch pump 210, 410.

Referring now to FIG. 5B, it can be seen that the first cannula 530 is coupled to a first reservoir 510A, while the second cannula 540 is coupled to a second reservoir 510B. Again, the infusion management unit (IMU) 220 or 420 may be configured to include the first and second cannulas 530, 540, each respectively coupled to the first and second reservoirs 510A, 510B.

Referring back to the Figures, while not shown, the patch pump 210, 410 within the scope of the present invention may include additional components that are configured to assist and/or improve the therapeutic agent delivery and analyte monitoring. Such additional components may include, but are not limited to, one or more power supplies such as batteries, one or more user input units (e.g., mechanical and/or electromechanical, button, switch, and the like), one or more user output units (e.g., a visual indicator, an audible alert, a vibratory alert, or a combination thereof), one or more additional redundant microprocessors to protect from failure modes of the patch pump 210, 410, or a leakage sensor for detecting any leakage of the therapeutic agent or any other fluid within the housing of the patch pump 210, 410 that may damage the internal components.

Accordingly, an integrated therapy management system in one embodiment includes a first cannula for transcutaneous placement under a skin layer of a patient at a first infusion site for a first time period, a second cannula for transcutaneous placement under the skin layer of the patient at a second infusion site for a second time period, and an analyte sensor configured for fluid contact with an analyte of the patient for a predetermined time period, where the first cannula and the second cannula are configured to deliver a therapeutic agent to the patient during the predetermined time period.

There may also be provided a housing, where the first cannula, the second cannula and the sensor are coupled to the housing.

Further, there may be provided a housing, where the first cannula and the sensor are coupled to the housing, and further, where the second cannula may be connected to the housing by an infusion tubing.

In one aspect, the first infusion site and the second infusion site may be separated by a predetermined distance.

Also, the predetermined time period may include approximately seven days.

The system may also include a reservoir coupled to the first cannula and the second cannula.

In a further aspect, there may be provided a first reservoir coupled to the first cannula, and a second reservoir coupled to the second cannula.

Moreover, when the second cannula is transcutaneously positioned, the first cannula may be withdrawn from the first infusion site.

The sensor may include an analyte sensor, and the therapeutic agent may include insulin.

A method in accordance with another embodiment includes positioning a portion of a first cannula under the skin of a patient, positioning a portion of a sensor under the skin of the patient, positioning a portion of a second cannula under the skin of a patient, and withdrawing the first cannula from the patient while retaining the sensor position under the skin of the patient.

The positioning of the portion of the first cannula and the positioning of the portion of the sensor may be substantially simultaneously performed.

In yet a further aspect, the sensor may be positioned under the skin of the patient for approximately seven days.

An integrated therapy management system in accordance with still another embodiment includes an on-body micropump including a first cannula for transcutaneous placement under a skin layer of a patient at a first infusion site for a first time period, a second cannula for transcutaneous placement under the skin layer of the patient at a second infusion site for a second time period, an analyte sensor configured for fluid contact with an analyte of the patient for a predetermined time period, and a controller in signal communication with the on-body micropump, the controller configured to transmit one or more signals to the micropump to control the delivery of a therapeutic agent to the patient using one or more of the first cannula and the second cannula.

The micropump may further include a transmitter unit operatively coupled to the analyte sensor.

The controller may be configured to receive one or more signals associated with one or more analyte levels of the patient from the transmitter unit.

In addition, the controller may be further configured to receive one or more signals associated with the therapeutic agent delivery.

Moreover, in yet a further aspect, the controller may be in signal communication with the on-body micropump over a wireless communication link.

A kit in yet a further embodiment includes a first cannula for transcutaneous placement under a skin layer of a patient at a first infusion site for a first time period, a second cannula for transcutaneous placement under the skin layer of the patient at a second infusion site for a second time period, and an analyte sensor configured for fluid contact with an analyte of the patient for a predetermined time period, where the first cannula and the second cannula are configured to deliver a therapeutic agent to the patient during the predetermined time period.

The kit may also include a housing, where the first cannula, the second cannula and the sensor are coupled to the housing.

Moreover, the kit may include a housing, where the first cannula and the sensor are coupled to the housing, and further, where second cannula may be connected to the housing by an infusion tubing.

In a further aspect, the kit may include a reservoir coupled to the first cannula and the second cannula, or alternatively, the kit may include a first reservoir coupled to the first cannula, and a second reservoir coupled to the second cannula.

Various other modifications and alterations in the structure and method of operation of this invention will be apparent to those skilled in the art without departing from the scope and spirit of the invention. Although the invention has been described in connection with specific preferred embodiments, it should be understood that the invention as claimed should not be unduly limited to such specific embodiments. It is intended that the following claims define the scope of the present invention and that structures and methods within the scope of these claims and their equivalents be covered thereby.

What is claimed is:

1. A method, comprising:
   positioning a portion of a first cannula under the skin of a patient for establishing a first fluid pathway for delivery of a therapeutic agent to within the patient;
   delivering the therapeutic agent to within the patient through the first cannula;
   positioning a portion of a sensor under the skin of the patient;
   automatically connecting a second cannula to a port of a fluid reservoir;
   automatically positioning a portion of the second cannula under the skin of a patient for establishing a second fluid pathway for delivery of the therapeutic agent to within the patient, the second cannula being wholly retained within a housing before the portion of the second cannula is automatically positioned under the skin of the patient;

delivering the therapeutic agent to within the patient through the second cannula; and automatically retracting the first cannula into the housing while retaining the sensor position under the skin of the patient;

wherein the withdrawing of the first cannula from the patient and the positioning the portion of the second cannula are performed such that delivery of the therapeutic agent to within the patient is continuous and uninterrupted while the first cannula is withdrawn and the second cannula is positioned.

2. The method of claim 1 wherein the positioning the portion of the first cannula and the positioning the portion of the sensor are substantially simultaneously performed.

3. The method of claim 1 wherein the sensor is positioned under the skin of the patient for approximately seven days.

4. The method of claim 1 wherein the sensor includes an analyte sensor.

5. The method of claim 1 wherein the withdrawing the first cannula from the patient and the positioning the portion of the second cannula are performed such that delivery of the therapeutic agent to within the patient is continuous.

6. The method of claim 1 wherein the withdrawing of the first cannula and the positioning of the second cannula are substantially simultaneously performed.

7. The method of claim 1 wherein the positioning of the portion of the second cannula is performed approximately mid-point in the usage life of the sensor.

8. The method of claim 7 wherein the usage life of the sensor is approximately 7 days.

9. The method of claim 1 wherein the therapeutic agent is contained within a reservoir, and wherein each of establishing the first fluid pathway and the second fluid pathway comprises connecting an infusion tubing between the reservoir and the first cannula and the second cannula, respectively.

10. The method of claim 1 wherein the portion of the first cannula is transcutaneously positioned through the skin of the patient at a first location, and the portion of the sensor is transcutaneously positioned through the skin of the patient at a second location, wherein the first location is spaced apart from the second location.

11. The method of claim 10 wherein the portion of the second cannula is transcutaneously positioned through the skin of the patient at a third location, wherein the third location is spaced apart from both the first location and the second location.

12. The method of claim 1 wherein withdrawing the first cannula from the patient is performed at a predetermined time during the usage life of the sensor, and wherein positioning of the portion of the second cannula is also performed at the predetermined time.

13. The method of claim 1 further comprising:

affixing a patch pump to the skin of the patient, wherein the patch pump comprises a housing, the first cannula, the sensor and the fluid reservoir containing the therapeutic agent;

wherein the first cannula is automatically retracted into the housing of the patch pump.

14. The method of claim 13 wherein the first cannula is wholly retained within the housing of the patch pump after the first cannula is retracted into the housing of the patch pump.

15. The method of claim 13 wherein the patch pump further comprises the second cannula that is wholly retained within the housing of the patch pump before the second cannula is positioned under the skin of the patient.

16. The method of claim 1 further comprising delivering the therapeutic agent to the patient through the first cannula and the second cannula according to a preprogrammed basal profile.

17. The method of claim 1 further comprising:

continuously detecting an analyte level in the interstitial fluid of the patient; and intermittently transmitting at periodic intervals data associated with the detected analyte level.

18. The method of claim 12 wherein the usage life of the sensor is longer than the usage life of the first cannula.

* * * * *